US011220429B2

(12) United States Patent
Skoulidas et al.

(10) Patent No.: US 11,220,429 B2
(45) Date of Patent: Jan. 11, 2022

(54) PROCESS INTENSIFICATION FOR REVERSE FLOW REACTORS

(71) Applicant: ExxonMobil Research and Engineering Company, Annandale, NJ (US)

(72) Inventors: Anastasios I. Skoulidas, Pittstown, NJ (US); Everett J. O'Neal, Asbury, NJ (US); Joseph E. Gatt, Annandale, NJ (US); Anjaneya S. Kovvali, Herndon, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 112 days.

(21) Appl. No.: 16/838,726

(22) Filed: Apr. 2, 2020

(65) Prior Publication Data
US 2021/0061657 A1 Mar. 4, 2021

Related U.S. Application Data

(60) Provisional application No. 62/891,638, filed on Aug. 26, 2019.

(51) Int. Cl.
*C01B 3/48* (2006.01)
*C07C 1/04* (2006.01)
*C07C 2/06* (2006.01)

(52) U.S. Cl.
CPC .............. *C01B 3/48* (2013.01); *C07C 1/0485* (2013.01); *C07C 2/06* (2013.01);
(Continued)

(58) Field of Classification Search
CPC .......... C07C 1/0485; C07C 2/06; C01B 3/48; C01B 3/2203; C01B 3/0233;
(Continued)

(56) References Cited

U.S. PATENT DOCUMENTS 6,159,395 A 12/2000 Early et al.
7,740,289 B2 1/2010 Tang
(Continued)

OTHER PUBLICATIONS

The International Search Report and Written Opinion for PCT/US2020/026404 dated Jun. 29, 2020.

*Primary Examiner* — Jafar F Parsa
(74) *Attorney, Agent, or Firm* — Liza Negron

(57) ABSTRACT

Systems and methods are provided for improving thermal management and/or efficiency of reaction systems including a reverse flow reactor for performance of at least one endothermic reaction and at least one supplemental exothermic reaction. The supplemental exothermic reaction can be performed in the recuperation zone of the reverse flow reactor system. By integrating the supplemental exothermic reaction into the recuperation zone, the heat generated from the supplemental exothermic reaction can be absorbed by heat transfer surfaces in the recuperation zone. The adsorbed heat can then be used to heat at least one of the fuel and the oxidant for the combustion reaction performed during regeneration, thus reducing the amount of combustion that is needed to achieve a desired temperature profile at the end of the regeneration step.

20 Claims, 3 Drawing Sheets

(52) U.S. Cl.
CPC ......... *C01B 2203/0233* (2013.01); *C01B 2203/0283* (2013.01); *C01B 2203/0811* (2013.01); *C01B 2203/0883* (2013.01); *C01B 2203/1241* (2013.01)

(58) Field of Classification Search
CPC ..... C01B 2203/0283; C01B 2203/0811; C01B 2203/0883; C01B 2203/1241; B01J 2208/0053
See application file for complete search history.

(56) References Cited

U.S. PATENT DOCUMENTS

| | | |
|---|---|---|
| 7,815,873 B2 | 10/2010 | Sankaranarayanan et al. |
| 8,754,276 B2 | 1/2014 | Buchanan et al. |
| 2005/0154060 A1* | 7/2005 | Deboeck .............. A61K 31/198 514/562 |
| 2012/0111315 A1 | 5/2012 | Grenda et al. |
| 2013/0270484 A1 | 10/2013 | Alizadeh-Khiavi et al. |
| 2017/0137285 A1 | 5/2017 | Ide et al. |

\* cited by examiner

PROCESS INTENSIFICATION FOR REVERSE FLOW REACTORS

CROSS REFERENCE TO RELATED APPLICATION

This application claims priority to U.S. Provisional Application Ser. No. 62/891,638 filed Aug. 26, 2019, which is herein incorporated by reference in its entirety.

FIELD

This invention relates to improved operation and thermal management in reverse flow reactors.

BACKGROUND

Reverse flow reactors are an example of a reactor type that is beneficial for use in processes with cyclic reaction conditions. For example, due to the endothermic nature of reforming reactions, additional heat needs to be introduced on a consistent basis into the reforming reaction environment. Reverse flow reactors can provide an efficient way to introduce heat into the reaction environment. After a portion of the reaction cycle used for reforming or another endothermic reaction, a second portion of the reaction cycle can be used for combustion or another exothermic reaction to add heat to the reaction environment in preparation for the next reforming step. U.S. Pat. Nos. 7,815,873 and 8,754,276 provide examples of using reverse flow reactors to perform various endothermic processes in a cyclic reaction environment. Due to the high temperatures used in endothermic processes, additional improvements to reverse flow reaction systems that provide increased thermal efficiency are desirable.

U.S. Pat. No. 7,740,289 describes production of synthesis gas in a reverse flow reactor by steam reforming followed by incomplete combustion of remaining hydrocarbons at elevated temperature and pressure. In addition to providing additional synthesis gas, the incomplete combustion provides heat to the reactor. In the method described in U.S. Pat. No. 7,740,289, the reversal of flow is achieved by alternating the end of the reactor used for input of the reactant flows for performing the steam reforming and incomplete combustion. The resulting synthesis gas can then be used for production of methanol.

U.S. Patent Application Publication 2012/0111315 describes an in-situ vaporizer and recuperator that is suitable for use with an alternating flow system, such as a pressure swing reformer.

SUMMARY

In various aspects, a method for operating a reverse flow reactor is provided. The method includes exposing at least a portion of a fuel mixture comprising fuel and 0.1 vol % or more of $O_2$ to at least one heated surface in a recuperation zone of a reverse flow reactor to heat the at least a portion of the fuel mixture. The method further includes reacting the fuel mixture under combustion conditions in the recuperation zone to form a flue gas and to heat one or more regeneration surfaces in a reaction zone of the reverse flow reactor to a regenerated surface temperature. The reaction zone can include a catalyst composition for an endothermic reaction. The recuperation zone can include a catalyst composition for a supplemental exothermic reaction. The method further includes exposing a reactant stream to the one or more regeneration surfaces in the reaction zone to increase a temperature of the reactant stream. The method further includes exposing, in the reaction zone, the reactant stream to the catalyst composition for the endothermic reaction under endothermic reaction conditions to form a product stream. A direction of flow for the reactant stream within the reaction zone can be reversed relative to a direction of flow for the fuel mixture. Additionally, the method can include exposing, in the recuperation zone, the product stream to the catalyst composition for the supplemental exothermic reaction under supplemental exothermic reaction conditions to form a reacted product stream and to heat the at least one heated surface in the recuperation zone.

In some aspects, an example of a catalyst composition for the endothermic reaction can be a reforming catalyst. In such aspects, the reactant stream can include a reformable hydrocarbon and steam, and the product stream can include hydrogen.

Examples of catalyst compositions for the supplemental exothermic reaction can include, but are not limited to, a water gas shift catalyst, a methanol synthesis catalyst, a methanol conversion catalyst, an olefin oligomerization catalyst, a Fischer-Tropsch catalyst for olefin production, or a combination thereof.

DETAILED DESCRIPTION

Figure 1:
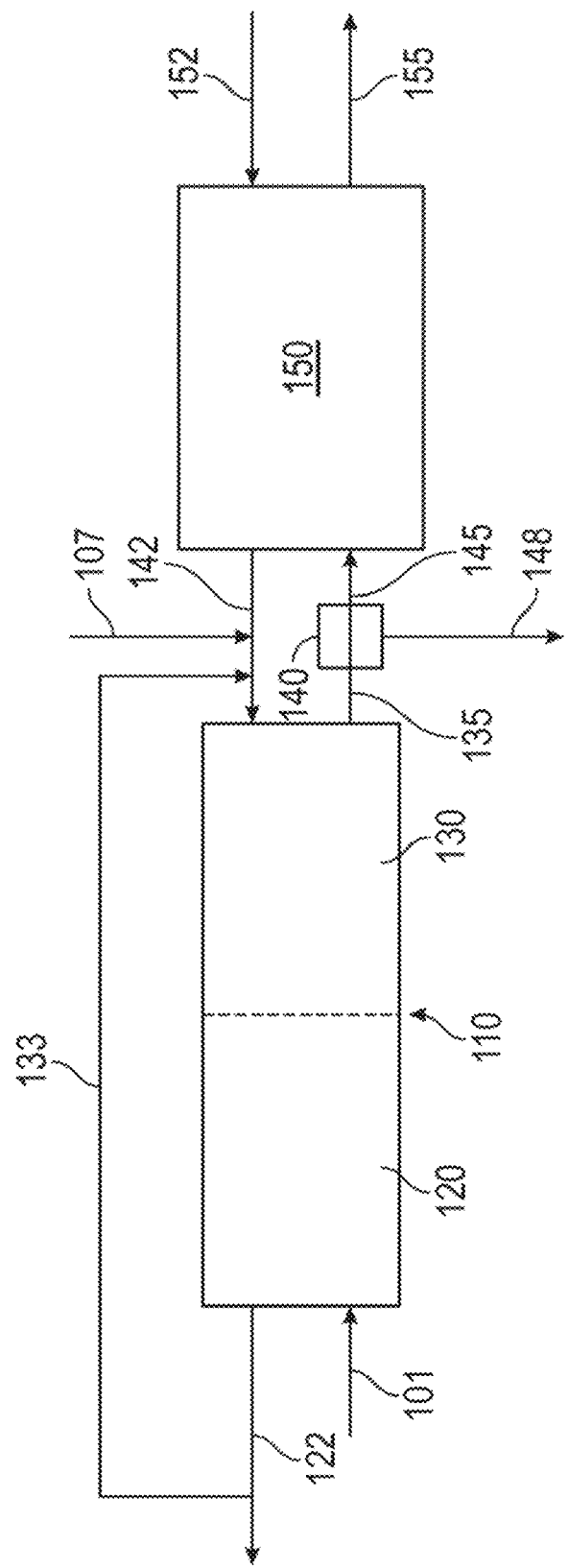
FIG. 1 shows an example of a configuration for reforming of hydrocarbons using a reverse flow reactor FIG. 2 schematically shows an example of operation of a reverse flow reactor.

All numerical values within the detailed description and the claims herein are modified by "about" or "approximately" the indicated value, and take into account experimental error and variations that would be expected by a person having ordinary skill in the art.

Overview

In various aspects, systems and methods are provided for improving thermal management and/or efficiency of reaction systems including a reverse flow reactor for performance of at least one endothermic reaction and at least one supplemental exothermic reaction. The supplemental exothermic reaction can be performed in the recuperation zone of the reverse flow reactor system. By integrating the supplemental exothermic reaction into the recuperation zone, the heat generated from the supplemental exothermic reaction can be absorbed by heat transfer surfaces in the recuperation zone. The adsorbed heat can then be used to heat at least one of the fuel and the oxidant for the combustion reaction performed during regeneration, thus reducing the amount of combustion that is needed to achieve a desired temperature profile at the end of the regeneration step. Additionally, integrating a supplemental exothermic reaction into a reverse flow reaction system can reduce or minimize the amount of heat that is lost and/or that needs to be recovered in a separate heat recovery step, such as by use of heat exchangers.

Reverse flow reactors and/or other reactors with flows in opposite directions at different stages of a reaction cycle can be useful when performing endothermic reactions at elevated temperatures. Examples of elevated temperatures correspond to 600° C. or more, or 800° C. or more, such as up to 1600° C. or possibly still higher. Various challenges in operating a reverse flow reactor are related to thermal management during a reaction cycle. For example, substantial amounts of energy are required for heating of input flows. Additionally, exhaust flows from reverse flow reactors contain substantial heat, which requires additional heat recovery. This includes exhaust flows corresponding to the products from the endothermic reaction, such as the synthesis gas product generated during reforming or olefin and aromatic products generated during dehydrogenation reactions. Such heat recovery steps often involve heat exchangers, which are limited in thermal efficiency.

During operation of a reverse flow reactor, a flow from a first direction, corresponding to a combustion or regeneration flow, can be used to heat a reaction zone within the reactor to a desired temperature. The reagents for a desired endothermic reaction can then be passed into the reactor using a flow in the opposite direction. The heat stored within the reactor during the regeneration step is used to provide heat for the desired endothermic reaction. The reaction products from the endothermic reaction can pass through a recuperation zone, where a portion of the heat from the reaction products is transferred to heat transfer surfaces in the recuperation zone. The heat stored in the recuperation zone can then be used to heat at least a portion of the combustion or regeneration flow.

In various aspects, additional heat can be recovered in the recuperation zone by performing a supplemental exothermic reaction on the product exhaust flow. Catalyst for the supplemental exothermic reaction can be integrated into the recuperation zone of the reverse flow reaction system. By performing the supplemental exothermic reaction in the recuperation zone, the heat generated by the supplemental exothermic reaction can be adsorbed by the heat transfer surfaces already present in the recuperator. The additional adsorbed heat can then be transferred to the fuel and/or oxidant used for the combustion reaction during regeneration.

Integrating a supplemental exothermic reaction into the recuperation zone can potentially provide several advantages. First, performing a supplemental exothermic reaction in the recuperation zone can reduce the number of distinct process elements that need to be maintained at an elevated temperature. Each distinct high temperature process element is susceptible to energy (thermal) loss to the environment, so reducing the number of high temperature process elements can improve overall thermal efficiency. Another advantage can be reducing or minimizing the number of heat exchangers that are needed to improve process efficiency. When a supplemental exothermic reaction is performed in a separate vessel, a separate heat exchanger is needed for heat recovery after both the primary reactor vessel and the vessel for the supplemental exothermic reaction. By contrast, performing the supplemental exothermic reaction in the recuperation zone allows a single heat exchange stage to be used for heat recovery from all of the reactions taking place in the primary reactor. As a result, the supplemental exothermic reaction can be performed prior to passing the exhaust from the reactor through an external heat exchange stage. Additionally, the heat transfer occurring within the recuperation zone correspond to direct heat transfers, where the material providing heat and the material receiving heat are in direct contact. This is in contrast to the indirect heat transfer that occurs in a heat exchanger, where heat from a first fluid is transferred through conduit or vessel walls in order to be passed into a second fluid.

The type of supplemental exothermic reaction that is performed can depend on the nature of the endothermic reaction. If hydrocarbon reforming is the endothermic reaction that is performed during a reaction cycle, one suitable supplemental exothermic reaction can be a high temperature water gas shift reaction to adjust the ratio of $H_2$ to CO in the synthesis gas generated by reforming. In this discussion, hydrocarbon reforming and the water gas shift reaction are used as examples of an endothermic reaction and supplemental exothermic reaction in order to illustrate the principles of the invention. It is understood that other convenient combinations of endothermic reaction and supplemental exothermic reaction can also be used. For example, another option can be to pair hydrocarbon reforming as an endothermic step with Fischer-Tropsch synthesis of olefins from the synthesis gas as an exothermic step. In such an aspect, the supplemental reaction can be performed in the presence of a catalyst suitable for synthesis of olefins via a Fischer-Tropsch process. Suitable catalysts for olefin production by a Fischer-Tropsch process include, for example, iron-based Fischer-Tropsch catalysts, such as a catalyst corresponding to iron particles supported on a non-reactive support and/or a manganese-promoted iron-based catalyst. As still another example, if alkane dehydrogenation is performed as the endothermic step, an olefin oligomerization can be performed as a supplemental exothermic step.

In this discussion, the reaction cycle in a reverse flow reactor can include a reaction step where an endothermic reaction is performed, and a regeneration step where a "primary" exothermic reaction is performed. The "primary" exothermic reaction corresponds to the combustion reaction that is used to heat the reaction zone during the regeneration step. The supplemental exothermic reaction corresponds to an exothermic reaction performed in the recuperation zone during the reaction step.

In this discussion, unless otherwise specified, all volume ratios correspond to volume ratios where the quantities in the ratio are specified based on volume at standard temperature and pressure (20° C., 100 kPa). This allows volume ratios to be specified consistently even though two flue gas volumes being compared may exist at different temperatures and pressures. When a volume ratio is specified for flue gases being delivered into a reactor, the corresponding flow rate of gas for a unit time under standard conditions can be used for the comparison.

Process Example—Reverse Flow Reforming and Regeneration with Integrated Water Gas Shift An example of an endothermic reaction that can be performed in a reverse flow reactor system is reforming of hydrocarbons under steam reforming conditions in the presence of $H_2O$, under dry reforming conditions in the presence of $CO_2$, or under conditions where both $H_2O$ and $CO_2$ are present in the reaction environment. As a general overview of operation during reforming in a swing reactor, such as a reverse flow reactor, a regeneration step or portion of a reaction cycle can be used to provide heat for the reactor. Reforming can then occur within the reactor during a reforming step or portion of the cycle, with the reforming reaction consuming heat provided during the reactor regeneration step. During reactor regeneration, fuel and an oxidant are introduced into the reactor from a regeneration end of the reactor. The fuel and oxidant pass through the recuperation zone as they travel from the regeneration end of the reactor toward the reaction zone. The bed and/or monoliths in the recuperation zone of the reactor can absorb heat, but typically do not include a catalyst for reforming. A catalyst for the supplemental exothermic reaction, however, can be included in the recuperation zone. As the fuel and oxidant pass through the recuperation zone, heat is transferred from the recuperation zone to the fuel and oxidant. Combustion does not occur immediately, but instead the location of combustion is controlled to occur in a middle portion of the reactor. The flow of the reactants continues during the regeneration step, leading to additional transfer of the heat generated from combustion into the reforming end (and therefore the reaction zone) of the reactor.

After a sufficient period of time, the combustion reaction is stopped. Any remaining combustion products and/or reactants can optionally be purged. The reforming step or portion of the reaction cycle can then start. The reactants for reforming can be introduced into the reforming end of the reactor, and thus flow in effectively the opposite direction relative to the flow during regeneration. The bed and/or monoliths in the reforming portion of the reactor can include a catalyst for reforming. In various aspects, at least a portion of the catalyst can correspond to a catalyst formed from a ceramic composition as described herein. As reforming occurs, the heat introduced into the reforming zone during combustion can be consumed by the endothermic reforming reaction. After exiting the reforming zone, the reforming products (and unreacted reactants) are no longer exposed to a reforming catalyst. As the reforming products pass through the recuperation zone, heat can be transferred from the products to the regeneration zone. Additionally, in aspects where a catalyst for a supplemental exothermic reaction is present, the supplemental exothermic reaction can be performed to generate additional heat. After a sufficient period of time, the reforming process can be stopped, remaining reforming products can optionally be collected or purged from the reactor, and the cycle can start again with a regeneration step.

The reforming reaction performed within the reactor can correspond reforming of methane and/or other hydrocarbons using steam reforming, in the presence of $H_2O$; using dry reforming, in the presence of $CO_2$, or using "bi" reforming in the presence of both $H_2O$ and $CO_2$. Examples of stoichiometry for steam, dry, and "bi" reforming of methane are shown in equations (1)-(3).

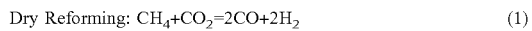

Dry Reforming: $CH_4+CO_2=2CO+2H_2$ (1)

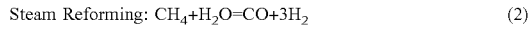

Steam Reforming: $CH_4+H_2O=CO+3H_2$ (2)

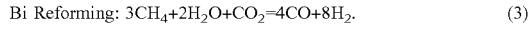

Bi Reforming: $3CH_4+2H_2O+CO_2=4CO+8H_2$. (3)

As shown in equations (1)-(3), dry reforming can produce lower ratios of $H_2$ to CO than steam reforming. Reforming reactions performed with only steam can generally produce a ratio of $H_2$ to CO of around 3, such as 2.5 to 3.5. By contrast, reforming reactions performed in the presence of $CO_2$ can generate much lower ratios, possibly approaching a ratio of $H_2$ to CO of roughly 1.0 or even lower. By using a combination of $CO_2$ and $H_2O$ during reforming, the reforming reaction can potentially be controlled to generate a wide variety of $H_2$ to CO ratios in a resulting syngas.

The reforming reactions shown in equations (1)-(3) are endothermic reactions. One of the challenges in commercial scale reforming can be providing the heat for performing the reforming reaction in an efficient manner while reducing or minimizing introduction of additional components into the desired synthesis gas product. Cyclic reaction systems, such as reverse flow reactor systems, can provide heat in a desirable manner by having a cycle including a reforming step and a regeneration step. During the regeneration step, combustion can be performed within a selected area of the reactor. A gas flow during regeneration can assist with transferring this heat from the combustion zone toward additional portions of the reforming zone in the reactor. The reforming step within the cycle can be a separate step, so that incorporation of products from combustion into the reactants and/or products from reforming can be reduced or minimized. The reforming step can consume heat, which can reduce the temperature of the reforming zone.

It is noted that the ratio of $H_2$ to CO in a synthesis gas can also be dependent on the water gas shift equilibrium. Although the stoichiometry in Equations (1)-(3) shows ratios of roughly 1 or roughly 3 for dry reforming and steam reforming, respectively, the equilibrium amounts of $H_2$ and CO in a synthesis gas can be different from the reaction stoichiometry. The equilibrium amounts can be determined based on the water gas shift equilibrium, which relates the concentrations of $H_2$, CO, $CO_2$ and $H_2O$ based on the reaction

$H_2O+CO<=>H_2+CO_2$ (4)

Most reforming catalysts, such as rhodium and/or nickel, can also serve as water gas shift catalysts. Thus, if reaction environment for producing $H_2$ and CO also includes $H_2O$ and/or $CO_2$, the initial stoichiometry from the reforming reaction may be altered based on the water gas shift equilibrium. However, this equilibrium is also temperature dependent, with higher temperatures favoring production of CO and $H_2O$. As a result, the ratio of $H_2$ to CO that is generated when forming synthesis gas is constrained by the water gas shift equilibrium at the temperature in the reaction zone when the synthesis gas is produced.

In order to further modify the ratio of CO to $H_2O$ in the synthesis gas, a separate high temperature water gas shift catalyst can be included in the recuperation zone of the reverse flow reactor. An example of a high temperature water gas shift catalyst is a catalyst including a mixture of iron oxide and chromium oxide. As described above, reforming catalysts as described herein can also provide water gas shift activity in a high temperature environment. The recuperation zone can be at a cooler temperature than the reaction zone, so that the water gas shift reaction will result in an increased amount of $H_2$ relative to CO. For example, the temperature in the reaction zone can be 600° C. or higher, while the temperature in the recuperation zone can be 300° C. to 450° C. Optionally, the equilibrium can be driven further toward production of $H_2$ by increasing the amount of water present in the diluent and/or decreasing the amount of $CO_2$ in the diluent.

By performing a supplemental water gas shift reaction (or another supplemental exothermic reaction) in the recuperation zone, several benefits can be achieved. First, as noted above, a potentially more favorable ratio of $H_2$ to CO can be achieved in the synthesis gas, due to performing water gas shift at a lower temperature than the reaction zone. Second, additional heat can be recovered for use in the subsequent regeneration step. In the water gas shift reaction, the formation of $H_2$ and $CO_2$ from $H_2O$ and CO is exothermic. Thus, in addition to adsorbing heat from the synthesis gas product, the recuperation zone can also adsorb heat released by the exothermic water gas shift reaction. Increasing the available heat in the recuperation zone can allow for a corresponding decrease in the amount of fuel that is combusted during regeneration. Third, performing the water gas shift reaction in the recuperation zone means that no additional vessel and/or reactor volume is maintained at elevated temperature. This reduces footprint for the reactor system while also reducing or minimizing heat lost to the environment.

One common source for methane is natural gas. In some applications, natural gas, including associated hydrocarbon and impurity gases, may be used as a feed for the reforming reaction. The supplied natural gas also may be sweetened and/or dehydrated natural gas. Natural gas commonly includes various concentrations of associated gases, such as ethane and other alkanes, preferably in lesser concentrations than methane. The supplied natural gas may include impurities, such as $H_2S$ and nitrogen. More generally, the hydrocarbon feed for reforming can include any convenient combination of methane and/or other hydrocarbons. Optionally, the reforming feed may also include some hydrocarbonaceous compounds, such as alcohols or mercaptans, which are similar to hydrocarbons but include one or more heteroatoms different from carbon and hydrogen. In some aspects, an additional component present in the feed can correspond to impurities such as sulfur that can adsorb to the catalytic monolith during a reducing cycle (such as a reforming cycle). Such impurities can be oxidized in a subsequent cycle to form sulfur oxide, which can then be reduced to release additional sulfur-containing components (or other impurity-containing components) into the reaction environment.

In some aspects, the feed for reforming can include, relative to a total weight of hydrocarbons in the feed for reforming, 5 wt % or more of $C_{2+}$ compounds, such as ethane or propane, or 10 wt % or more, or 15 wt % or more, or 20 wt % or more, such as up to 50 wt % or possibly still higher. It is noted that nitrogen and/or other gases that are non-reactive in a combustion environment, such as $H_2O$ and $CO_2$, may also be present in the feed for reforming. In aspects where the reformer corresponds to an on-board reforming environment, such non-reactive products can optionally be introduced into the feed, for example, based on recycle of an exhaust gas into the reformer. Additionally or alternately, the feed for reforming can include 40 wt % or more methane, or 60 wt % or more, or 80 wt % or more, or 95 wt % or more, such as having a feed that is substantially composed of methane (98 wt % or more). In aspects where the reforming corresponds to steam reforming, a molar ratio of steam molecules to carbon atoms in the feed can be 0.3 to 4.0. It is noted that methane has 1 carbon atom per molecule while ethane has 2 carbon atoms per molecule. In aspects where the reforming corresponds to dry reforming, a molar ratio of $CO_2$ molecules to carbon atoms in the feed can be 0.05 to 3.0.

Within the reforming zone of a reverse flow reactor, the temperature can vary across the zone due to the nature of how heat is added to the reactor and/or due to the kinetics of the reforming reaction. The highest temperature portion of the zone can typically be found near a middle portion of the reactor. This middle portion can be referred to as a mixing zone where combustion is initiated during regeneration. At least a portion of the mixing zone can correspond to part of the reforming zone if a monolith with reforming catalyst extends into the mixing zone. As a result, the location where combustion is started during regeneration can typically be near to the end of the reforming zone within the reactor. It is noted that the location of combustion catalyst within the reactor(s) can overlap with the location of reforming catalyst within the reactor(s), so that some portions of the reactor(s) can correspond to both combustion zone and reaction zone. Moving from the center of the reactor to the ends of the reactor, the temperature can decrease. As a result, the temperature at the beginning of the reforming zone (at the end of the reactor) can be cooler than the temperature at the end of the reforming zone (in the middle portion of the reactor).

As the reforming reaction occurs, the temperature within the reforming zone can be reduced. The rate of reduction in temperature can be related to the kinetic factors of the amount of available hydrocarbons for reforming and/or the temperature at a given location within the reforming zone. As the reforming feed moves through the reforming zone, the reactants in the feed can be consumed, which can reduce the amount of reforming that occurs at downstream locations. However, the increase in the temperature of the reforming zone as the reactants move across the reforming zone can lead to an increased reaction rate.

At roughly 500° C., the reaction rate for reforming can be sufficiently reduced that little or no additional reforming will occur. As a result, in some aspects as the reforming reaction progresses, the beginning portion of the reforming zone can cool sufficiently to effectively stop the reforming reaction within a portion of the reforming zone. This can move the location within the reactor where reforming begins to a location that is further downstream relative to the beginning of the reforming zone. When a sufficient portion of the reforming zone has a temperature below 500° C., or below 600° C., the reforming step within the reaction cycle can be stopped to allow for regeneration. Alternatively, based on the amount of heat introduced into the reactor during regeneration, the reforming portion of the reaction cycle can be stopped based on an amount of reaction time, so that the amount of heat consumed during reforming (plus heat lost to the environment) is roughly in balance with the amount of heat added during regeneration. After the reforming process is stopped, any remaining synthesis gas product still in the reactor can optionally be recovered prior to starting the regeneration step of the reaction cycle.

The regeneration process can then be initiated. During regeneration, a fuel such as methane, natural gas, or $H_2$, and oxygen can be introduced into the reactor and combusted. The location where the fuel and oxidant are allowed to mix can be controlled in any convenient manner, such as by introducing the fuel and oxidant via separate channels. By delaying combustion during regeneration until the reactants reach a central portion of the reactor, the non-reforming end of the reactor can be maintained at a cooler temperature. This can also result in a temperature peak in a middle portion of the reactor. The temperature peak can be located within a portion of the reactor that also includes the reforming catalyst. During a regeneration cycle, the temperature within the reforming reactor can be increased sufficiently to allow for the reforming during the reforming portion of the cycle. This can result in a peak temperature within the reactor of 1100° C. or more, or 1200° C. or more, or 1300° C. or more, or potentially a still higher temperature.

The relative length of time and reactant flow rates for the reforming and regeneration portions of the process cycle can be selected to balance the heat provided during regeneration with the heat consumed during reforming. For example, one option can be to select a reforming step that has a similar length to the regeneration step. Based on the flow rate of hydrocarbons, $H_2O$, and/or $CO_2$ during the reforming step, an endothermic heat demand for the reforming reaction can be determined. This heat demand can then be used to calculate a flow rate for combustion reactants during the regeneration step. Of course, in other aspects the balance of heat between reforming and regeneration can be determined in other manners, such as by determining desired flow rates for the reactants and then selecting cycle lengths so that the heat provided by regeneration balances with the heat consumed during reforming.

In addition to providing heat, the reactor regeneration step during a reaction cycle can also allow for coke removal from the catalyst within the reforming zone. In various aspects, one or more types of catalyst regeneration can potentially occur during the regeneration step. One type of catalyst regeneration can correspond to removal of coke from the catalyst. During reforming, a portion of the hydrocarbons introduced into the reforming zone can form coke instead of forming CO or $CO_2$. This coke can potentially block access to the catalytic sites (such as metal sites) of the catalyst. In some aspects, the rate of formation can be increased in portions of the reforming zone that are exposed to higher temperatures, such as portions of the reforming zone that are exposed to temperatures of 800° C. or more, or 900° C. or more, or 1000° C. or more. During a regeneration step, oxygen can be present as the temperature of the reforming zone is increased. At the temperatures achieved during regeneration, at least a portion of the coke generated during reforming can be removed as CO or $CO_2$.

Due to the variation in temperature across the reactor, several options can be used for characterizing the temperature within the reactor and/or within the reforming zone of the reactor. One option for characterizing the temperature can be based on an average bed or average monolith temperature within the reforming zone. In practical settings, determining a temperature within a reactor requires the presence of a measurement device, such as a thermocouple. Rather than attempting to measure temperatures within the reforming zone, an average (bed or monolith) temperature within the reforming zone can be defined based on an average of the temperature at the beginning of the reforming zone and a temperature at the end of the reforming zone. Another option can be to characterize the peak temperature within the reforming zone after a regeneration step in the reaction cycle. Generally, the peak temperature can occur at or near the end of the reforming zone, and may be dependent on the location where combustion is initiated in the reactor. Still another option can be to characterize the difference in temperature at a given location within the reaction zone at different times within a reaction cycle. For example, a temperature difference can be determined between the temperature at the end of the regeneration step and the temperature at the end of the reforming step. Such a temperature difference can be characterized at the location of peak temperature within the reactor, at the entrance to the reforming zone, at the exit from the reforming zone, or at any other convenient location.

In various aspects, the reaction conditions for reforming hydrocarbons can include one or more of an average reforming zone temperature ranging from 400° C. to 1200° (or more); a peak temperature within the reforming zone of 800° C. to 1500° C.; a temperature difference at the location of peak temperature between the end of a regeneration step and the end of the subsequent reforming step of 25° C. or more, or 50° C. or more, or 100° C. or more, or 200° C. or more, such as up to 800° C. or possibly still higher; a temperature difference at the entrance to the reforming zone between the end of a regeneration step and the end of the subsequent reforming step of 25° C. or more, or 50° C. or more, or 100° C. or more, or 200° C. or more, such as up to 800° C. or possibly still higher; and/or a temperature difference at the exit from the reforming zone between the end of a regeneration step and the end of the subsequent reforming step of 25° C. or more, or 50° C. or more, or 100° C. or more, or 200° C. or more, such as up to 800° C. or possibly still higher.

With regard to the average reforming zone temperature, in various aspects the average temperature for the reforming zone can be 500° C. to 1500° C., or 400° C. to 1200° C., or 800° C. to 1200° C., or 400° C. to 900° C., or 600° C. to 1100° C., or 500° C. to 1000° C. Additionally or alternately, with regard to the peak temperature for the reforming zone (likely corresponding to a location in the reforming zone close to the location for combustion of regeneration reactants), the peak temperature can be 800° C. to 1500° C., or 1000° C. to 1400° C., or 1200° C. to 1500° C., or 1200° C. to 1400° C.

Additionally or alternately, the reaction conditions for reforming hydrocarbons can include a pressure of 0 psig to 1500 psig (10.3 MPa), or 0 psig to 1000 psig (6.9 MPa), or 0 psig to 550 psig (3.8 MPa); and a gas hourly space velocity of reforming reactants of 1000 $hr^{-1}$ to 50,000 $hr^{-1}$. The space velocity corresponds to the volume of reactants relative to the volume of monolith per unit time. The volume of the monolith is defined as the volume of the monolith as if it was a solid cylinder.

In some aspects, an advantage of operating the reforming reaction at elevated temperature can be the ability to convert substantially all of the methane and/or other hydrocarbons in a reforming feed. For example, for a reforming process where water is present in the reforming reaction environment (i.e., steam reforming or bi-reforming), the reaction conditions can be suitable for conversion of 10 wt % to 100 wt % of the methane in the reforming feed, or 20 wt % to 80 wt %, or 50 wt % to 100 wt %, or 80 wt % to 100 wt %, or 10 wt % to 98 wt %, or 50 wt % to 98 wt %. Additionally or alternately, the reaction conditions can be suitable for conversion of 10 wt % to 100 wt % of the hydrocarbons in the reforming feed, or 20 wt % to 80 wt %, or 50 wt % to 100 wt %, or 80 wt % to 100 wt %, or 10 wt % to 98 wt %, or 50 wt % to 98 wt %

In other aspects, for a reforming process where carbon dioxide is present in the reforming reaction environment (i.e., dry reforming or bi-reforming), the reaction conditions can be suitable for conversion of 10 wt % to 100 wt % of the methane in the reforming feed, or 20 wt % to 80 wt %, or 50 wt % to 100 wt %, or 80 wt % to 100 wt %, or 10 wt % to 98 wt %, or 50 wt % to 98 wt %. Additionally or alternately, the reaction conditions can be suitable for conversion of 10 wt % to 100 wt % of the hydrocarbons in the reforming feed, or 20 wt % to 80 wt %, or 50 wt % to 100 wt %, or 80 wt % to 100 wt %, or 10 wt % to 98 wt %, or 50 wt % to 98 wt %.

In some alternative aspects, the reforming reaction can be performed under dry reforming conditions, where the reforming is performed with $CO_2$ as a reagent but with a reduced or minimized amount of $H_2O$ in the reaction environment. In such alternative aspects, a goal of the reforming reaction can be to produce a synthesis gas with a $H_2$ to CO ratio of 1.0 or less. In some aspects, the temperature during reforming can correspond to the temperature ranges described for steam reforming. Optionally, in some aspects a dry reforming reaction can be performed at a lower temperature of between 500° C. to 700° C., or 500° C. to 600° C. In such aspects, the ratio of $H_2$ to CO can be 0.3 to 1.0, or 0.3 to 0.7, or 0.5 to 1.0. Performing the dry reforming reaction under these conditions can also lead to substantial coke production, which can require removal during regeneration in order to maintain catalytic activity.

FIG. 1 shows an example of a configuration for using a reverse flow reactor as part of a reaction system for hydrogen production. In the example shown in FIG. 1, a single reverse flow reactor and a single hydrogen recovery stage are shown for clarity. It is understood that any convenient number of reverse flow reactors can be used in conjunction with any convenient number of hydrogen recovery stages, so that continuous production of hydrogen can be performed even though the reverse flow reactor and the hydrogen recovery stage can have separate reaction cycles that include a regeneration step.

In the example configuration shown in FIG. 1, the reverse flow reactor 110 is used to perform steam reforming as the endothermic reaction. The feed 101 for the endothermic reaction to corresponds to methane and steam. The feed 101 is introduced into reverse flow reactor 110 at the end of the reactor that is closest to reaction zone 120. During the reaction (reforming) step of the reaction cycle, the feed is reformed to generate hydrogen and carbon monoxide. The reforming effluent passes through recuperation zone 130 prior to leaving the reactor. In recuperation zone 130, the reforming effluent is exposed to a high temperature water gas shift catalyst that increases the relative ratio of hydrogen to carbon monoxide in the effluent. The shifted effluent 135 is then exhausted from reactor 110. The shifted effluent 135 is then passed into a heat exchanger stage 140 to recover heat. For example, heat can be recovered as steam 148. The cooled effluent 145 can then be passed into a hydrogen recovery stage 150, such as a pressure swing adsorber, to allow for generation of a high purity hydrogen stream 155.

After a period of time, production of hydrogen stream 155 can be stopped to allow for regeneration of reverse flow reactor 110 and hydrogen recovery stage 150. In the idealized example shown in FIG. 1, the regeneration step for the hydrogen recovery stage 150 can occur at the same time as the regeneration step for reverse flow reactor 110. In other aspects, valving can be used to allow the reaction cycle(s) for one or more hydrogen recovery stages 150 to be independent from the reaction cycle(s) for one or more reverse flow reactors.

During the regeneration step, a purge stream 152 is introduced into hydrogen recovery stage (e.g., pressure swing adsorber) 150 to generate a tail gas 142. The tail gas can include, for example, CO as well as unreacted methane that was present in the reforming effluent. Additional fuel 107 can be added to the tail gas 142. Optionally, a recycle stream 133 of $CO_2$ and/or $H_2O$ can also be added as a diluent gas for the regeneration step. The combined stream of tail gas 142, additional fuel 107, and optional recycle stream 133 can then be passed into the end of reactor 110 that is closer to recuperation zone 130. The combined stream is heated in recuperation zone 130, and then combusted at or near the interface between recuperation zone 130 and reaction zone 120. A portion of the resulting combustion effluent 122 that is exhausted from reactor 110 can be used to form the optional recycle stream 133.

Example of Reverse Flow Reactor Configuration

For endothermic reactions operated at elevated temperatures, such as hydrocarbon reforming, a reverse flow reactor can provide a suitable reaction environment for providing the heat for the endothermic reaction.

In a reverse flow reactor, the heat needed for an endothermic reaction may be provided by creating a high-temperature heat bubble in the middle of the reactor. A two-step process can then be used wherein heat is (a) added to the reactor bed(s) or monolith(s) via in-situ combustion, and then (b) removed from the bed in-situ via an endothermic process, such as reforming, pyrolysis, or steam cracking. This type of configuration can provide the ability to consistently manage and confine the high temperature bubble in a reactor region(s) that can tolerate such conditions long term. A reverse flow reactor system can allow the primary endothermic and regeneration processes to be performed in a substantially continuous manner.

In some aspects, a reverse flow reactor system can correspond to a single reactor with a reaction zone and a recuperation zone. In other aspects, a reverse flow reactor system can include first and second reactors, oriented in a series relationship with each other with respect to a common flow path, and optionally but preferably along a common axis. The common axis may be horizontal, vertical, or otherwise.

During a regeneration step, reactants (e.g., fuel and oxygen) are permitted to combine or mix in a reaction zone to combust therein, in-situ, and create a high temperature zone or heat bubble inside a middle portion of the reactor system. The heat bubble can correspond to a temperature that is at least about the initial temperature for the endothermic reaction. Typically, the temperature of the heat bubble can be greater than the initial temperature for the endothermic reaction, as the temperature will decrease as heat is transferred from the heat bubble in a middle portion of the reactor toward the ends of the reactor. In some aspects, the combining can be enhanced by a reactant mixer that mixes the reactants to facilitate substantially complete combustion/reaction at the desired location, with the mixer optionally located between the first and second reactors. The combustion process can take place over a long enough duration that the flow of first and second reactants through the first reactor also serves to displace a substantial portion, (as desired) of the heat produced by the reaction (e.g., the heat bubble), into and at least partially through the second reactor, but preferably not all of the way through the second reactor to reduce or minimize waste of heat and overheating the second reactor. This heat is transferred, for example, to one or more surfaces in the second reactor and/or in the reaction zone for the endothermic reaction in a reactor. The flue gas may be exhausted through the second reactor, but preferably most of the heat is retained within the second reactor. The amount of heat displaced into the second reactor during the regeneration step can also be limited or determined by the desired exposure time or space velocity that the hydrocarbon feed gas will have in the endothermic reaction environment. In aspects where a single reactor is used, the heat produced by the reaction can be displaced into and/or at least partially through the reaction zone of the reactor, but preferably the displacement can also reduce or minimize waste of heat due to exit of heated gas from the reactor.

After regeneration or heating the second reactor media (which can include and/or correspond to one or more surfaces including a catalyst for an endothermic reaction), in the next/reverse step or cycle, reactants for the endothermic reaction methane (and/or natural gas and/or another hydrocarbon) can be supplied or flowed through the second reactor, from the direction opposite the direction of flow during the heating step. For example, in a reforming process, methane (and/or natural gas and/or another hydrocarbon) can be supplied or flowed through the second reactor. The methane can contact the hot second reactor and mixer media, in the heat bubble region, to transfer the heat to the methane for reaction energy.

Figure 2:
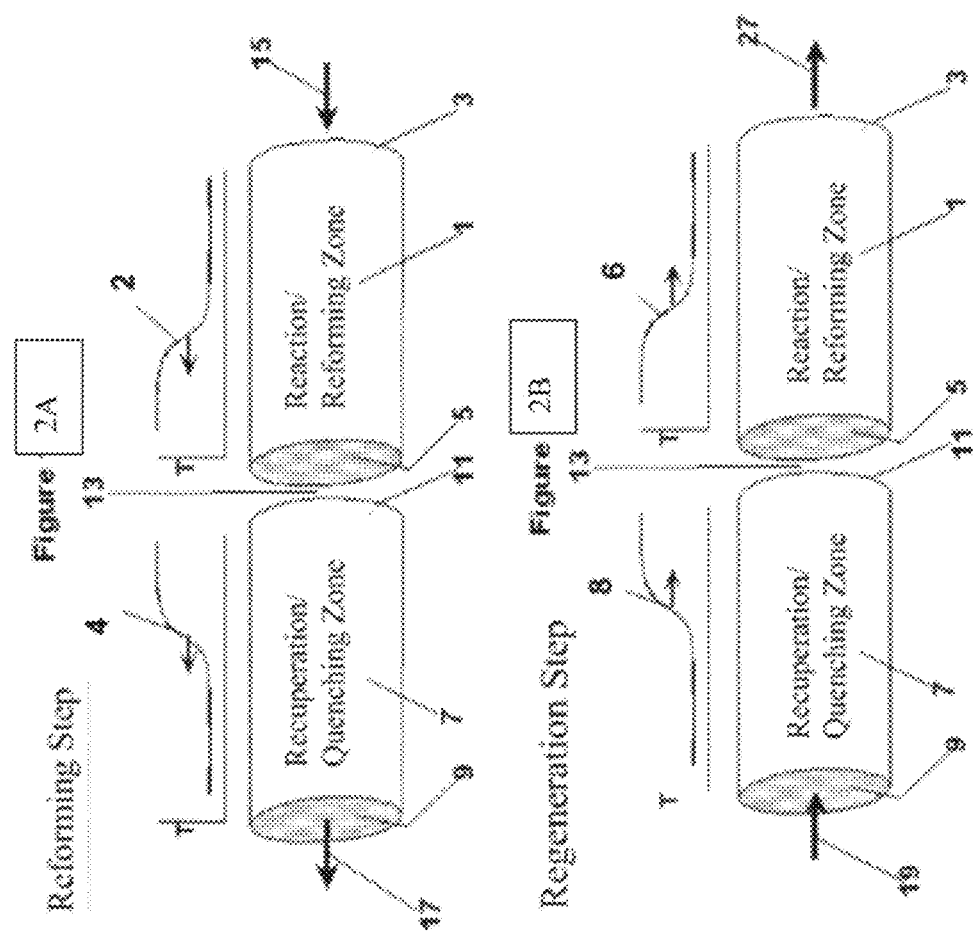

For some aspects, the basic two-step asymmetric cycle of a reverse flow regenerative bed reactor system is depicted in FIGS. 2A and 2B of FIG. 2 in terms of a reactor system having two zones/reactors; a first or recuperator/quenching zone (7) and a second or reaction zone (1). Both the reaction zone (1) and the recuperation zone (7) can contain regenerative monoliths and/or other regenerative structures formed from a doped ceramic composition. Regenerative monoliths or other regenerative structures, as used herein, comprise materials that are effective in storing and transferring heat as well as being effective for carrying out a chemical reaction. The regenerative monoliths and/or other structures can correspond to any convenient type of material that is suitable for storing heat, transferring heat, and catalyzing a reaction. Examples of structures can include bedding or packing material ceramic beads or spheres, ceramic honeycomb materials, ceramic tubes, extruded monoliths, and the like, provided they are competent to maintain integrity, functionality, and withstand long term exposure to temperatures in excess of 1200° C., or in excess of 1400° C., or in excess of 1600° C., which can allow for some operating margin. In some aspects, the catalytic ceramic monolith and/or other catalytic ceramic structure can be used without the presence of an additional washcoat.

To facilitate description of FIG. 2, the reactor is described herein with reference to a reforming reaction. It is understood that other convenient types of endothermic reactions can generally be performed using a reverse flow reactor, such as the reactor shown in FIG. 2.

As shown in FIG. 2B of FIG. 2, at the beginning of the "reaction" step of the cycle, a secondary end 5 of the reaction zone 1 (a.k.a. herein as the second reactor) can be at an elevated temperature as compared to the primary end 3 of the reaction zone 1, and at least a portion (including the first end 9) of the recuperator or quench zone 7 (a.k.a. herein as the first reactor), can be at a lower temperature than the reaction zone 1 to provide a quenching effect for the resulting product. In an aspect where the reactors are used to perform reverse flow reforming, a methane-containing reactant feed (or other hydrocarbon-containing reactant feed) can be introduced via a conduit(s) 15, into a primary end 3 of the reforming or reaction zone 1. In various aspects, the hydrocarbon-containing reactant feed can also contain $H_2O$, $CO_2$, or a combination thereof.

The feed stream from inlet(s) 15 can absorb heat from reaction zone 1 and endothermically react to produce the desired synthesis gas product. As this step proceeds, a shift in the temperature profile 2, as indicated by the arrow, can be created based on the heat transfer properties of the system. When the ceramic catalyst monolith/other catalyst structure is designed with adequate heat transfer capability, this profile can have a relatively sharp temperature gradient, which gradient can move across the reaction zone 1 as the reforming step proceeds. In some aspects, a sharper temperature gradient profile can provide for improved control over reaction conditions. In aspects where another type of endothermic reaction is performed, a similar shift in temperature profile can occur, so that a temperature gradient moves across reaction zone 1 as the reaction step proceeds.

The effluent from the reforming reaction, which can include unreacted feed components (hydrocarbons, $H_2O$, $CO_2$) as well as synthesis gas components, can exit the reaction zone 1 through a secondary end 5 at an elevated temperature and pass through the recuperator reactor 7, entering through a second end 11, and exiting at a first end 9. The recuperator 7 can initially be at a lower temperature than the reaction zone 1. As the products (and optionally unreacted feed) from the reforming reaction pass through the recuperation zone 7, the gas can be quenched or cooled to a temperature approaching the temperature of the recuperation zone substantially at the first end 9, which in some embodiments can be approximately the same temperature as the regeneration feed introduced via conduit 19 into the recuperator 7 during the second step of the cycle. As the reforming effluent is cooled in the recuperation zone 7, a temperature gradient 4 can be created in the zone's regenerative bed(s) and can move across the recuperation zone 7 during this step. The quenching can heat the recuperator 7, which can be cooled again in the second step to later provide another quenching service and to prevent the size and location of the heat bubble from growing progressively through the quench reactor 7. After quenching, the reaction gas can exit the recuperator at 9 via conduit 17 and can be processed for separation and recovery of the various components. In some aspects, a catalyst for a supplemental exothermic reaction can also be included in the recuperation zone 7. In such aspects, at least a portion of the additional heat generated by the supplemental exothermic reaction can also be transferred to the regenerative beds in the recuperation zone 7. For example, the catalyst can correspond to a high temperature water gas shift catalyst, so that the exothermic water gas shift reaction can occur in the recuperation zone. Examples of high temperature water gas shift catalysts include catalysts based on iron oxide and/or chromium oxide.

The second step of the cycle, referred to as the regeneration step, can then begin with reintroduction of the first and second regeneration reactants via conduit(s) 19. The first and second reactants can pass separately through hot recuperator 7 toward the second end 11 of the recuperator 7, where they can be combined for exothermic reaction or combustion in or near a central region 13 of the reactor system.

An example of the regeneration step is illustrated in FIG. 2B of FIG. 2. Regeneration can entail transferring recovered sensible heat from the recuperation zone 7 to the reaction zone 1 to thermally regenerate the reaction beds 1 for the subsequent reaction cycle. Regeneration gas/reactants can enter recuperation zone 7, such as via conduit(s) 19, and flow through the recuperation zone 7 and into the reaction zone 1. In doing so, the temperature gradients 6 and 8 may move across the beds as illustrated by the arrows on the exemplary graphs in FIG. 2B, similar to but in opposite directions to the graphs of the temperature gradients developed during the reaction cycle in FIG. 2A of FIG. 2. Fuel and oxidant reactants may combust at a region proximate to the interface 13 of the recuperation zone 7 and the reaction zone 1. The heat recovered from the recuperation zone together with the heat of combustion can be transferred to the reaction zone, thermally regenerating the regenerative reaction monoliths and/or beds 1 disposed therein.

In some aspects, several of the conduits within a channel may convey a mixture of first and second reactants, due at least in part to some mixing at the first end (17) of the first reactor. However, the numbers of conduits conveying combustible mixtures of first and second reactants can be sufficiently low such that the majority of the stoichiometrically reactable reactants will not react until after exiting the second end of the first reactor. The axial location of initiation of combustion or exothermic reaction within those conduits conveying a mixture of reactants can be controlled by a combination of temperature, time, and fluid dynamics. Fuel and oxygen usually require a temperature-dependent and mixture-dependent autoignition time to combust. Still though, some reaction may occur within an axial portion of the conduits conveying a mixture of reactants. However, this reaction can be acceptable because the number of channels having such reaction can be sufficiently small that there is only an acceptable or inconsequential level of effect upon the overall heat balance within the reactor. The design details of a particular reactor system can be selected so as to avoid mixing of reactants within the conduits as much as reasonably possible.

Figure 3:
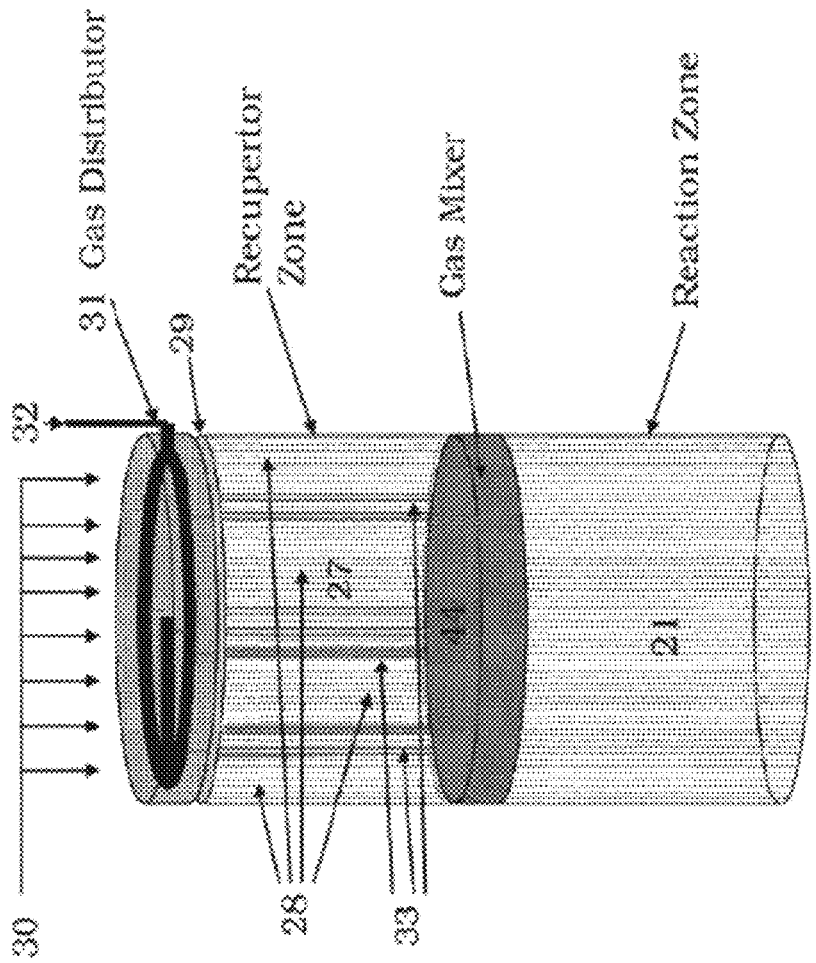
FIG. 3 schematically shows an example of a reverse flow reactor.

FIG. 3 illustrates another exemplary reactor system that may be suitable in some applications for controlling and deferring the combustion of fuel and oxidant to achieve efficient regeneration heat. FIG. 3 depicts a single reactor system, operating in the regeneration cycle. The reactor system may be considered as comprising two reactors zones. The recuperator 27 can be the zone primarily where quenching takes place and provides substantially isolated flow paths or channels for transferring both of the quenching reaction gases through the reactor media, without incurring combustion until the gasses arrive proximate or within the reactor core 13 in FIG. 2. In some aspects, such channels can also reduce or minimize exposure of the fuel and/or oxidant to the catalyst for the supplemental exothermic reaction. The reformer 2 can be the reactor where regeneration heating and methane (and/or hydrocarbon) reformation primarily occurs, and may be considered as the second reactor for purposes herein. Although the first and second reactors in the reactor system are identified as separately distinguishable reactors, it is understood that the first and second reactors may be manufactured, provided, or otherwise combined into a common single reactor bed, whereby the reactor system might be described as comprising merely a single reactor that integrates both cycles within the reactor. The terms "first reactor" and "second reactor" can merely refer to the respective zones within the reactor system whereby each of the regeneration, reformation, quenching, etc., steps take place and do not require that separate components be utilized for the two reactors. However, various aspects can comprise a reactor system whereby the recuperator reactor includes conduits and channels as described herein, and the reformer reactor may similarly possess conduits. Additionally or alternatively, some aspects may include a reformer reactor bed that is arranged different from and may even include different materials from, the recuperator reactor bed.

As discussed previously, the first reactor or recuperator 27 can include various gas conduits 28 for separately channeling two or more gases following entry into a first end 29 of the recuperator 27 and through the regenerative bed(s) disposed therein. A first gas 30 can enter a first end of a plurality of flow conduits 28. In addition to providing a flow channel, the conduits 28 can also comprise effective flow barriers (e.g., which effectively function such as conduit walls) to prevent cross flow or mixing between the first and second reactants and maintain a majority of the reactants effectively separated from each other until mixing is permitted. As discussed previously, each of the first and second channels can comprise multiple channels or flow paths. The first reactor may also comprise multiple substantially parallel flow segments, each comprising segregated first and second channels.

In some aspects, the recuperator can be comprised of one or more extruded honeycomb monoliths, as described above. Each monolith may provide flow channel(s) (e.g., flow paths) for one of the first or second reactants. Each channel preferably includes a plurality of conduits. Alternatively, a monolith may comprise one or more channels for each reactant with one or more channels or groups of conduits dedicated to flowing one or more streams of a reactant, while the remaining portion of conduits flow one or more streams of the other reactant. It is recognized that at the interface between channels, a number of conduits may convey a mixture of first and second reactant, but this number of conduits is proportionately small.

In aspects where a monolith is used, the monolith can have any convenient shape suitable for use as a catalytic surface. An example of a monolith can be an extruded honeycomb monolith. Honeycomb monoliths can be extruded structures that comprise many (e.g., a plurality, meaning more than one) small gas flow passages or conduits, arranged in parallel fashion with thin walls in between. A small reactor may include a single monolith, while a larger reactor can include a number of monoliths, while a still larger reactor may be substantially filled with an arrangement of many honeycomb monoliths. Each monolith may be formed by extruding monolith blocks with shaped (e.g., square or hexagonal) cross-section and two- or three-dimensionally stacking such blocks above, behind, and beside each other. Monoliths can be attractive as reactor internal structures because they provide high heat transfer capacity with minimum pressure drop.

In some aspects, honeycomb monoliths can be characterized as having open frontal area (or geometric void volume) between 25% and 55%, and having conduit density between 50 and 2000 pores or cells per square inch (CPSI), or between 100 and 900 cells per square inch, or between 100 cells per square inch to 600 cells per square inch. For example, in one embodiment, the conduits may have a diameter/characteristic cell side length of only a few millimeters, such as on the order of roughly one millimeter. Reactor media components, such as the monoliths or alternative bed media, can provide for channels that include a packing with an average wetted surface area per unit volume that ranges from 50 ft$^{-1}$ to 3000 ft$^{-1}$ (~0.16 km$^{-1}$ to ~10 km$^{-1}$), or from 100 ft$^{-1}$ to 2500 ft$^{-1}$ (~0.32 km$^{-1}$ to ~8.2 km$^{-1}$), or from 200 ft$^{-1}$ to 2000 ft$^{-1}$ (~0.65 km$^{-1}$ to ~6.5 km$^{-1}$), based upon the volume of the first reactor that is used to convey a reactant. These relatively high surface area per unit volume values can aid in achieving a relatively quick change in the temperature through the reactor, such as generally illustrated by the relatively steep slopes in the exemplary temperature gradient profile graphs shown in FIG. 2A or 2B of FIG. 2.

Reactor media components can also provide for channels that include a packing that includes a high volumetric heat transfer coefficient (e.g., 0.02 cal/cm$^3$ s° C. or more, or 0.05 cal/cm$^3$ s° C. or more, or 0.10 cal/cal/cm$^3$ s° C. or more); that have low resistance to flow (low pressure drop); that have an operating temperature range consistent with the highest temperatures encountered during regeneration; that have high resistance to thermal shock; and/or that have high bulk heat capacity (e.g., 0.10 cal/cm$^3$ s° C. or more, or 0.20 cal/cm$^3$ s° C. or more). As with the high surface area values, these relatively high volumetric heat transfer coefficient values and/or other properties can aid in achieving a relatively quick change in the temperature through the reactor, such as generally illustrated by the relatively steep slopes in the exemplary temperature gradient profile graphs, such as in FIGS. 2A and 2B of FIG. 2. The cited values are averages based upon the volume of reactor used for conveyance of a reactant.

In various aspects, adequate heat transfer rate can be characterized by a heat transfer parameter, ATHT, below 500° C., or below 100° C., or below 50° C. The parameter ATHT, as used herein, is the ratio of the bed-average volumetric heat transfer rate that is needed for recuperation, to the volumetric heat transfer coefficient of the bed, hv. The volumetric heat transfer rate (e.g. cal/cm$^3$ sec) that is sufficient for recuperation can be calculated as the product of the gas flow rate (e.g. g/sec) with the gas heat capacity (e.g. cal/g° C.) and desired end-to-end temperature change (excluding any reaction, e.g. ° C.), and then this quantity can be divided by the volume (e.g. cm$^3$) of the reactor (or portion of a reactor) traversed by the gas. The volumetric heat transfer coefficient of the bed, hv, can typically be calculated as the product of an area-based coefficient (e.g. cal/cm$^2$ s° C.) and a specific surface area for heat transfer (av, e.g. cm$^2$/cm$^3$), often referred to as the wetted area of the packing.

In some aspects, a washcoat can be added to the formed, sintered ceramic composition prior to exposing the composition to a reducing environment to form dopant metal particles. A washcoat can allow the sintered ceramic composition to be impregnated with additional catalytic metal. Such additional catalytic metal can be the same as the dopant metal or different.

One option for incorporating an additional catalytic metal into a washcoat can be to impregnate a catalyst support with the additional catalytic metal, such as by impregnation via incipient wetness. The impregnation can be performed with an aqueous solution of suitable metal salt or other catalytic metal precursor, such as tetramineplatinum nitrate or rhodium nitrate hydrate. The impregnated support can then be dried and/or calcined for decomposition of the catalytic metal precursor. A variety of temperature profiles can potentially be used for the heating steps. One or more initial drying steps can be used for drying the support, such as heating at a temperature from 100° C. to 200° C. for 0.5 hours to 24 hours. A calcination to decompose the catalytic metal precursor compound can be at a temperature of 200° C. to 800° C. for 0.5 hours to 24 hours, depending on the nature of the impregnated catalytic metal compound. Depending on the precursor for the catalytic metal, the drying step(s) and/or the decomposing calcination step(s) can be optional. Examples of additional catalytic metals can include, but are not limited to, Ni, Co, Fe, Pd, Rh, Ru, Pt, Ir, Cu, Ag, Au, Zr, Cr, Ti, V, W, Mo, Nb, Mn, Sr, La, and combinations thereof.

Alternative embodiments may use reactor media other than monoliths, such as whereby the channel conduits/flow paths may include a more tortuous pathways (e.g. convoluted, complex, winding and/or twisted but not linear or tubular), including but not limited to labyrinthine, variegated flow paths, conduits, tubes, slots, and/or a pore structure having channels through a portion(s) of the reactor and may include barrier portion, such as along an outer surface of a segment or within sub-segments, having substantially no effective permeability to gases, and/or other means suitable for preventing cross flow between the reactant gases and maintaining the first and second reactant gases substantially separated from each other while axially transiting the recuperator 27. Such other types of reactor media can be suitable, so long as at least a portion of such media can be formed by sintering a ceramic catalytic composition as described herein, followed by exposing such media to reducing conditions to activate the catalyst. For such embodiments, the complex flow path may create a lengthened effective flow path, increased surface area, and improved heat transfer. Such design may be preferred for reactor embodiments having a relatively short axial length through the reactor. Axially longer reactor lengths may experience increased pressure drops through the reactor. However for such embodiments, the porous and/or permeable media may include, for example, at least one of a packed bed, an arrangement of tiles, a permeable solid media, a substantially honeycomb-type structure, a fibrous arrangement, and a mesh-type lattice structure.

In some aspects, the reverse flow reactor can include some type of equipment or method to direct a flow stream of one of the reactants into a selected portion of the conduits. In the exemplary embodiment of FIG. 3, a gas distributor 31 can direct a second gas stream 32 to second gas stream channels that are substantially isolated from or not in fluid communication with the first gas channels, here illustrated as channels 33. The result can be that at least a portion of gas stream 33 is kept separate from gas stream 30 during axial transit of the recuperator 27. In some aspects, the regenerative bed(s) and/or monolith(s) of the recuperation zone can comprise channels having a gas or fluid barrier that isolates the first reactant channels from the second reactant channels. Thereby, both of the at least two reactant gases that transit the channel means may fully transit the regenerative bed(s), to quench the regenerative bed, absorb heat into the reactant gases, before combining to react with each other in the combustion zone.

In various aspects, gases (including fluids) 30 and 32 can each comprise a component that reacts with a component in the other reactant 30 and 32, to produce an exothermic reaction when combined. For example, each of the first and second reactant may comprise one of a fuel gas and an oxidant gas that combust or burn when combined with the other of the fuel and oxidant. By keeping the reactants substantially separated, the location of the heat release that occurs due to exothermic reaction can be controlled. In some aspects "substantially separated" can be defined to mean that at least 50 percent, or at least 75 percent, or at least 90 percent of the reactant having the smallest or limiting stoichiometrically reactable amount of reactant, as between the first and second reactant streams, has not become consumed by reaction by the point at which these gases have completed their axial transit of the recuperator 27. In this manner, the majority of the first reactant 30 can be kept isolated from the majority of the second reactant 32, and the majority of the heat release from the reaction of combining reactants 30 and 32 can take place after the reactants begin exiting the recuperator 27. The reactants can be gases, but optionally some reactants may comprise a liquid, mixture, or vapor phase.

The percent reaction for these regeneration streams is meant the percent of reaction that is possible based on the stoichiometry of the overall feed. For example, if gas 30 comprised 100 volumes of air (80 volumes N2 and 20 Volumes O$_2$), and gas 32 comprised 10 volumes of hydrogen, then the maximum stoichiometric reaction would be the combustion of 10 volumes of hydrogen (H$_2$) with 5 volumes of oxygen (02) to make 10 volumes of H$_2$O. In this case, if 10 volumes of hydrogen were actually combusted in the recuperation zone (27), this would represent 100% reaction of the regeneration stream. This is despite the presence of residual un-reacted oxygen, because in this example the un-reacted oxygen was present in amounts above the stoichiometric requirement. Thus, in this example the hydrogen is the stoichiometrically limiting component. Using this definition, less than 50% reaction, or less than 25% reaction, or less than 10% reaction of the regeneration streams can occur during the axial transit of the recuperator (27).

In various aspects, channels 28 and 33 can comprise ceramic (including zirconia), alumina, or other refractory material capable of withstanding temperatures exceeding 1200° C., or 1400° C., or 1600° C. Additionally or alternately, channels 28 and 33 can have a wetted area between 50 ft$^{-1}$ and 3000 ft$^{-1}$, or between 100 ft$^{-1}$ and 2500 ft$^{-1}$, or between 200 ft$^{-1}$ and 2000 ft$^{-1}$.

Referring again briefly to FIG. 2, the reactor system can include a first reactor 7 containing a first end 9 and a second end 11, and a second reactor 1 containing a primary end 3 and a secondary end 5. The embodiments illustrated in FIGS. 2 and 3 are merely simple illustrations provided for explanatory purposes only and are not intended to represent a comprehensive embodiment. Reference made to an "end" of a reactor merely refers to a distal portion of the reactor with respect to an axial mid-point of the reactor. Thus, to say that a gas enters or exits an "end" of the reactor, such as end 9, means merely that the gas may enter or exit substantially at any of the various points along an axis between the respective end face of the reactor and a mid-point of the reactor, but more preferably closer to the end face than to the mid-point. Thereby, one or both of the first and second reactant gases could enter at the respective end face, while the other is supplied to that respective end of the reactor through slots or ports in the circumferential or perimeter outer surface on the respective end of the reactor.

Additional Embodiments

Embodiment 1. A method for operating a reverse flow reactor, comprising: exposing at least a portion of a fuel mixture comprising fuel and 0.1 vol % or more of $O_2$ to at least one heated surface in a recuperation zone of a reverse flow reactor to heat the at least a portion of the fuel mixture; reacting the fuel mixture under combustion conditions in the recuperation zone to form a flue gas and to heat one or more regeneration surfaces in a reaction zone of the reverse flow reactor to a regenerated surface temperature, the reaction zone comprising a catalyst composition for an endothermic reaction, the recuperation zone comprising a catalyst composition for a supplemental exothermic reaction; exposing a reactant stream to the one or more regeneration surfaces in the reaction zone to increase a temperature of the reactant stream; exposing, in the reaction zone, the reactant stream to the catalyst composition for the endothermic reaction under endothermic reaction conditions to form a product stream, a direction of flow for the reactant stream within the reaction zone being reversed relative to a direction of flow for the fuel mixture; exposing, in the recuperation zone, the product stream to the catalyst composition for the supplemental exothermic reaction under supplemental exothermic reaction conditions to form a reacted product stream and to heat the at least one heated surface in the recuperation zone.

Embodiment 2. The method of Embodiment 1, wherein the catalyst composition for the endothermic reaction comprises a reforming catalyst.

Embodiment 3. The method of Embodiment 2, wherein the reactant stream comprises a reformable hydrocarbon and steam, and wherein the product stream comprises hydrogen, the reformable hydrocarbon optionally comprising methane.

Embodiment 4. The method of any of the above embodiments, wherein the catalyst composition for the supplemental exothermic reaction comprises a water gas shift catalyst.

Embodiment 5. The method of Embodiment 4, wherein the water gas shift catalyst comprises a high temperature water gas shift catalyst, a second reforming catalyst that is optionally different from the reforming catalyst in the reaction zone, or a combination thereof.

Embodiment 6. The method of any of Embodiments 1-3, wherein the catalyst composition for the supplemental exothermic reaction comprises a methanol synthesis catalyst, a methanol conversion catalyst, or a combination thereof.

Embodiment 7. The method of any of Embodiments 1-3, wherein the catalyst composition for the supplemental exothermic reaction comprises an olefin oligomerization catalyst.

Embodiment 8. The method of any of Embodiments 1-3, wherein the catalyst composition for the supplemental exothermic reaction comprises a Fischer-Tropsch catalyst for olefin production.

Embodiment 9. The method of any of the above embodiments, wherein the fuel mixture is combusted downstream from the catalyst composition for the supplemental exothermic reaction relative to the direction of flow for the fuel mixture.

Embodiment 10. The method of any of the above embodiments, wherein at least one of the fuel and the $O_2$ is not exposed to the catalyst composition for the supplemental exothermic reaction.

Embodiment 11. The method of any of the above embodiments, wherein the product stream is exposed to the catalyst composition for the supplemental exothermic reaction prior to being passed into an external heat exchange stage.

Embodiment 12. The method of any of the above embodiments, wherein the flue gas comprises a temperature of 420° C. or more.

Embodiment 13. The method of any of the above embodiments, wherein the endothermic reaction conditions comprise a temperature of 600° C. or more.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for operating a reverse flow reactor, comprising:
   exposing at least a portion of a fuel mixture comprising fuel and 0.1 vol % or more of $O_2$ to at least one heated surface in a recuperation zone of a reverse flow reactor to heat the at least a portion of the fuel mixture;
   reacting the fuel mixture under combustion conditions in the recuperation zone to form a flue gas and to heat one or more regeneration surfaces in a reaction zone of the reverse flow reactor to a regenerated surface temperature, the reaction zone comprising a catalyst composition for an endothermic reaction, the recuperation zone comprising a catalyst composition for a supplemental exothermic reaction;
   exposing a reactant stream to the one or more regeneration surfaces in the reaction zone to increase a temperature of the reactant stream;
   exposing, in the reaction zone, the reactant stream to the catalyst composition for the endothermic reaction under endothermic reaction conditions to form a product stream, a direction of flow for the reactant stream within the reaction zone being reversed relative to a direction of flow for the fuel mixture;
   exposing, in the recuperation zone, the product stream to the catalyst composition for the supplemental exothermic reaction under supplemental exothermic reaction conditions to form a reacted product stream and to heat the at least one heated surface in the recuperation zone.

2. The method of claim 1, wherein the catalyst composition for the endothermic reaction comprises a reforming catalyst.

3. The method of claim 2, wherein the reactant stream comprises a reformable hydrocarbon and steam, and wherein the product stream comprises hydrogen.

4. The method of claim 3, wherein the reformable hydrocarbon comprises methane.

5. The method of claim 1, wherein the catalyst composition for the supplemental exothermic reaction comprises a water gas shift catalyst.

6. The method of claim 5, wherein the water gas shift catalyst comprises a high temperature water gas shift catalyst.

7. The method of claim 5, wherein the water gas shift catalyst comprises a second reforming catalyst.

8. The method of claim 1, wherein the catalyst composition for the supplemental exothermic reaction comprises a methanol synthesis catalyst, a methanol conversion catalyst, or a combination thereof.

9. The method of claim 1, wherein the catalyst composition for the supplemental exothermic reaction comprises an olefin oligomerization catalyst.

10. The method of claim 1, wherein the catalyst composition for the supplemental exothermic reaction comprises a Fischer-Tropsch catalyst for olefin production.

11. The method of claim 1, wherein the fuel mixture is combusted downstream from the catalyst composition for the supplemental exothermic reaction relative to the direction of flow for the fuel mixture.

12. The method of claim 1, wherein at least one of the fuel and the $O_2$ is not exposed to the catalyst composition for the supplemental exothermic reaction.

13. The method of claim 1, wherein the product stream is exposed to the catalyst composition for the supplemental exothermic reaction prior to being passed into an external heat exchange stage.

14. The method of claim 1, wherein the flue gas comprises a temperature of 420° C. or more.

15. The method of claim 1, wherein the endothermic reaction conditions comprise a temperature of 600° C. or more.

16. A method for reforming hydrocarbons, comprising:
exposing at least a portion of a fuel mixture comprising fuel and 0.1 vol % or more of $O_2$ to at least one heated surface in a recuperation zone of a reverse flow reactor to heat the at least a portion of the fuel mixture;
reacting the fuel mixture under combustion conditions in the recuperation zone to form a flue gas comprising a temperature of 420° C. or more, and to heat one or more regeneration surfaces in a reaction zone of the reverse flow reactor to a regenerated surface temperature, the reaction zone comprising a reforming catalyst, the recuperation zone comprising a water gas shift catalyst;
exposing a reactant stream comprising at least one hydrocarbon to the one or more regeneration surfaces in the reaction zone to increase a temperature of the reactant stream;
exposing, in the reaction zone, the reactant stream to the reforming catalyst under reforming conditions to form a product stream comprising a first ratio of $H_2$ and CO, a direction of flow for the reactant stream within the reaction zone being reversed relative to a direction of flow for the fuel mixture;
exposing, in the recuperation zone, the product stream to a water gas shift catalyst under water gas shift reaction conditions to form a reacted product stream comprising a second ratio of $H_2$ to CO and to heat the at least one heated surface in the recuperation zone, the second ratio being greater than the first ratio.

17. The method of claim 16, further comprising:
passing the reacted product stream into a heat exchange stage to form a cooled reacted product stream; and
separating a hydrogen-containing stream from the cooled reacted product stream.

18. The method of claim 16, wherein the water gas shift catalyst comprises a high temperature water gas shift catalyst.

19. The method of claim 16, wherein the water gas shift catalyst comprises a second reforming catalyst is different from the reforming catalyst in the reaction zone.

20. The method of claim 16, wherein at least one of the fuel and the $O_2$ is not exposed to the catalyst composition for the supplemental exothermic reaction.

* * * * *